United States Patent [19]

Scales

[11] Patent Number: 4,586,932

[45] Date of Patent: May 6, 1986

[54] ENDOPROSTHETIC BONE DEVICES

[75] Inventor: John T. Scales, Stanmore, England

[73] Assignee: National Research Development Corp., London, England

[21] Appl. No.: 592,009

[22] Filed: Mar. 21, 1984

[30] Foreign Application Priority Data

Apr. 12, 1983 [GB] United Kingdom ............ 8309844

[51] Int. Cl.⁴ .............................................. A61F 2/28
[52] U.S. Cl. ...................................... 623/16; 623/18; 623/22
[58] Field of Search .................... 3/1.9, 1.91, 1.911, 3/1.912, 1.913, 1; 128/92 BC, 92 C, 92 A; 269/266

[56] References Cited

U.S. PATENT DOCUMENTS 4,376,384  3/1983  Brown et al. ...................... 269/266

Primary Examiner—Richard J. Apley
Assistant Examiner—James Prizant
Attorney, Agent, or Firm—Cushman, Darby & Cushman

[57] ABSTRACT

In order to provide for lengthening of a long bone, such as in place of natural growth, an endoprosthetic device (10, 20) is provided in a two-part telescopic form defining a longitudinal passageway (15) in which ball bearings (40) are progressively locatable to control adjustably the device length. At least one end (24) of the device will be adapted for securement in the bone, and the other end (11) can be similarly adapted or define an articulation surface for a joint. The telescoped parts are preferably mutually keyed (22, 23) against rotation, the passageway is preferably of like cross-sectional form as the ball bearings so that the latter form a singular sequence therein, and the ball bearings are suitably located by way of an acutely inclined branch passageway (17).

10 Claims, 3 Drawing Figures

U.S. Patent    May 6, 1986    4,586,932
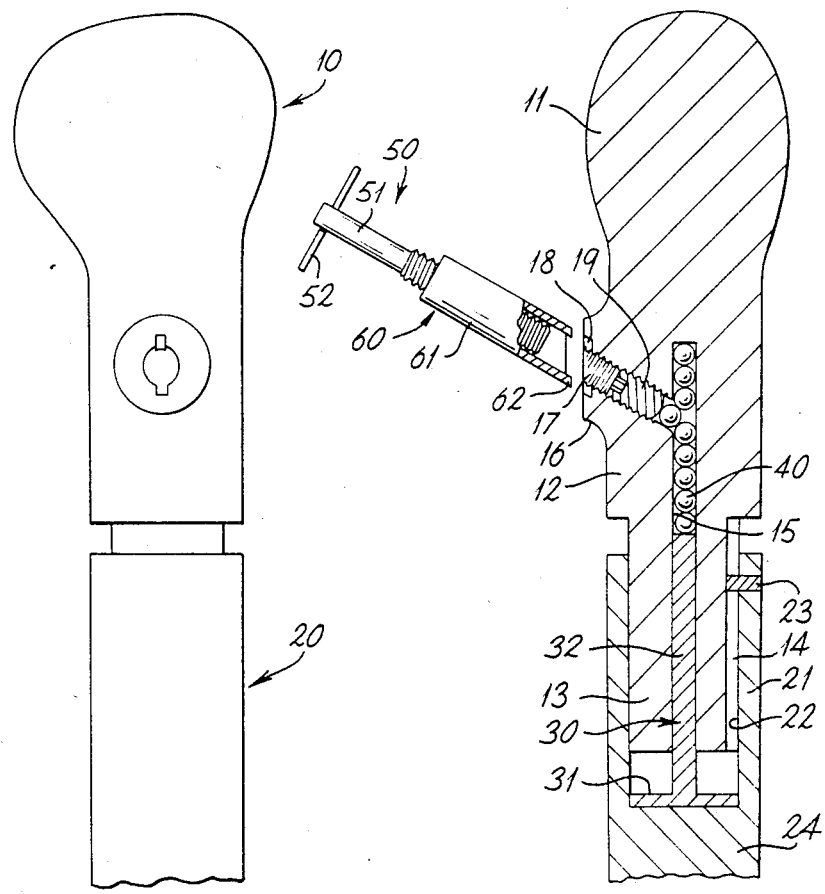
Fig. 1
Fig. 2
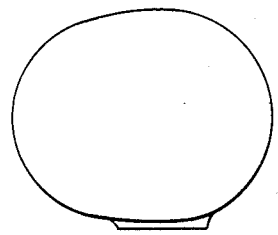
Fig. 3

ENDOPROSTHETIC BONE DEVICES

This invention concerns endoprosthetic bone devices and more particularly, but not exclusively, for use in children.

The use of an endoprosthetic bone joint device in a child is generally regarded as temporary. This view arises from two factors. Firstly, the joint will normally involve a long bone, and growth in long bone is from its ends where a so-called growth plate of cartilagenic material progressively ossifies and moves on longitudnally until final coalescent ossification at maturity. Secondly, current designs of device commonly involve a component which seats on the end of the long bone and includes a stem which passes longitudinally into the bone for the purposes of component securement. Clearly, in application to a child, this component will pass through the growth plate with the result that continuing growth will act to move the component away from its securement and loosen the same.

It has been proposed in a copending Patent Application (UK No. 8307820 filed Mar. 22, 1983 which forms the priority basis for Scales et al U.S. Ser. No. 592,084, filed Mar. 22, 1984, now refiled as Ser. No. 693,824 on Jan. 23, 1985) to improve this situation by the provision of an endoprosthetic bone joint device comprising a component for a long bone and including two parts, of which one part seats on one end of the bone and has a stem to pass longitudinally into the bone, and of which the other part is in the general form of a tubular socket adapted to receive such stem in sliding engagement and for securement with the bone remote from said one end. In application to a child the stemmed part can move with growth of the bone end on which it is seated because it is not directly secured with the bone on the other side of the growth plate, but instead simply passes through this plate to be stabilised by its stem engagement in the secured socket.

Clearly this last device is of limited application insofar as its extensibility, as just described, is passively dependent on natural growth. However, other situations can arise in which natural growth no longer continues in a bone for which elongation is desirable and a prosthetic device is required which can not only accommodate but in fact assist in inducing such elongation.

For this last purpose the present invention provides an endoprosthetic device for a long bone which device comprises a component of elongate form including two parts in longitudinal telescopic engagement defining therebetween a passageway of length variable with said engagement, one of said parts having a transverse opening affording access to said passageway, a releasable closure member for said opening, and a plurality of ball bearings locatable in said passageway by way of said opening to control adjustably the extent of said telescopic engagement.

In practice the proposed component will normally form part of a bone joint involving the relevant long bone, with the free end of one of the two component parts being formed to provide an appropriate articulation capability. In this case it will often be unnecessary for the one component part to be secured with bone, its location being determined by its engagement with the other component part and by the action of other natural elements of the joint and its capsule. The other component part will, of course, normally be secured to bone and it can be specially adapted for this purpose to accord with established techniques.

Notwithstanding this expected normal situation, the proposed component can be applied as a mid-shaft prosthesis in a long bone in which case both parts will be directly secured with opposite end portions of the bone.

In development of the proposed component to date certain features of value have emerged which it is useful to note.

The two component parts are preferably interengaged in a keyed or equivalent manner to inhibit mutual rotation about the longitudinal axis of the bone.

The passageway between the two component parts is preferably of circular cross-sectional shape of substantially the same diameter as the ball bearings so that the latter form a single sequence along the passageway. This reduces the number of ball bearings required compared to what is otherwise necessary for a given bearing diameter and, at the same time, allows the engaged portions to be thicker than otherwise possible to enhance mechanical strength.

In this last case, the transverse opening preferably joins the passageway by way of a branch passageway inclined relative thereto at an acute angle and of corresponding cross-sectional shape. This inclination is found to facilitate addition to the ball bearing sequence in the main passageway in order to extend the telescopic engagement.

Also the telescopic arrangement is preferably of a compound form with the two component parts already mentioned having respective male and female formations in mutual sliding engagement, the male formation having a bore therein to define the passageway, and a piston member having its head seated in the female formation and its rod slidably engaged in the bore. This arrangement allows the overall thickness apart from the passageway to be apportioned between the two component parts independently of the passageway diameter, which is not the case if these parts directly define the passageway by their mutual engagement.

A fuller understanding of the invention and presently preferred features thereof can be gathered from consideration of one embodiment thereof illustrated, by way of example, with reference to the accompanying drawings, in which:

FIGS. 1, 2 and 3 schematically show the embodiment respectively in a side view, a longitudinal sectional view, and an end view.

The embodiment is in fact a component for the use in the upper part of the humerus which articulates with the scapula in the shoulder joint. The component comprises two main parts 10 and 20 of which the first completely replaces the relevant end portion of the bone and assumes its articulation function, while the second part is secured in the remanent natural bone to hold the first part in adjustable telescopic engagement therewith.

The first component part 10 has an elongated body which is asymetrically enlarged over one end portion 11 to a convexly rounded shape simulating the humeral head at the shoulder. The part 10 progresses from portion 11 through an intermediate portion 12 terminating in a stepped reduction to a circular cylindrical shaping over its other end portion or male formation 13. This last portion 13 has a longitudinal slot 14 over at least the major part of its length from the free end thereof. The portion 13 also has an axial bore 15 therein extending from its free end into the intermediate portion 12.

The intermediate portion 12 is locally enlarged to form a plateau-like protrusion 16 projecting in a direction generally transverse to that of maximum enlargement in the portion 11. This protrusion has an internally threaded bore 17 passing therethrough to communicate at an acute angle with the axial bore 15 partway along the latter, the bore 17 having corresponding diameter to bore 15. The bore 17 joins at its mouth in the protrusion with two like diametrically-opposed notches 18 and the bore can be closed by a threaded plug 19.

The second component part 20 also has an elongated body of which one end portion 21 has a female formation by being longitudinally hollowed at 22 from its free end in a cylindrical shaping complementary with that of the first part end portion 13 for sliding engagement of the former portion in the latter. In this last connection the end portion 21 also has a radially inwardly projecting stud 23 adjacent to its free end, which stud engages in the slot 14 to inhibit rotation in the sliding engagement.

The other end portion 24 of the second component part 20 is adapted for intramedullary securement in the humerus in any established manner and will normally be generally tapered for this purpose.

Interengagement of the two component parts 10 and 20 involves an additional subsidiary part 30 in the form of a piston. The head 31 of this last part slidably seats in the hollow 22 between the base of the latter and the free end of the first part portion 13, while the piston rod 32 slidably engages in the bore 15. The piston rod is at least as long as the hollow so as to be engaged in the bore 15 for all positions of engagement between the component parts 10 and 20, but the bore 15 is longer than the rod so as always to leave a portion of the former available to serve as the passageway referred to earlier, the associated branch passageway being formed by the bore 17. It will be evident that the component parts 10 and 20 when assembled as shown with the piston 30 therein form a compound telescopic arrangement in which the passageway and main component parts are extensible in unison.

The component as so far described is, of course, completed by a plurality of ball bearings for location in the passageway of bore 15. The relevant balls are denoted at 40 in the bore, they are of substantially equal diameter with the bore to form a singular sequence therein, and they are secured in position by the plug 19. In use of the component the part 20 is secured in the humerus to locate part 10 with its portion 11 appropriately located for articulation with the glenoid cavity of the scapula, sufficient balls 40 having been secured in the bore 15 to constrain the component to a suitable minimum length when the parts 10 and 20 are freely engaged prior to completion of the surgical procedure and consequent application of muscular forces acting to compress the component.

At some later time when it becomes appropriate to extend the component to simulate growth of the humerus, additional balls 40 are individually progressively added to the sequence. This is effected by way of bore 17 which is accessible transcutaneously by relatively minor surgery to expose the protrusion 16 whereby the plug 19 can be released.

Addition of a ball in these last circumstances will, of course, require sufficient force to overcome the natural compressive forces acting on the component. The necessary force can be applied by way of the plug itself but it is found preferable to use an ancilliary instrument such as shown at 50. The instrument 50 comprises a threaded rod 51 to substitute for the plug, the rod having a T-bar lever 52 at its outer end. Also, it is found convenient to employ a guide as shown at 60 for the instrument 50, which guide can also facilitate entry of a ball to the bore 17. This guide 60 comprises a tubular sleeve member 61 having at one end a pair of diametrically-opposed lugs 62 to engage in the notches 18 at the mouth of the bore 17.

It is useful to note the finding in practice that forcible addition to the sequence of balls can cause sufficient distortion in the latter to wedge the same in the bore 15 against automatic loosening upon release of the instrument 50 for plug replacement, but without further extending adjustment being made unduly difficult.

I claim:

1. An endoprosthetic device for a long bone which device comprises:
    a component of elongate form for use as an endoprothesis in a long bone and including two parts in longitudinal telescopic engagement defining therebetween a passageway of length variable with said engagement,
    one of said parts having a transverse opening affording access to said passageway, a releasable closure member for said opening, and
    a plurality of ball bearings located in said passageway by way of said opening to control adjustably the extent of said telescopic engagement.

2. A device according to claim 1 wherein at least one of said two parts has an end remote from said telescopic engagement structured for securement in bone.

3. A device according to claim 2 wherein the other of said two parts has a respective end remote from said telescopic engagement shaped to approximate the natural articulation surface at one end of said bone.

4. A device according to claim 1 wherein said two parts are mutually keyed to inhibit rotation therebetween about the longitudinal direction of said telescopic engagement.

5. A device according to claim 1 wherein said passageway is of circular cross-sectional shape and said ball bearings are of substantially the same diameter as said shape.

6. A device according to claim 5 wherein said opening joins said passageway by way of a branch passageway inclined relative thereto at an acute angle and of corresponding diameter.

7. A device according to claim 6 wherein said branch passageway is internally threaded, and said closure member is in the form of a threaded plug engageable in said branch passageway.

8. A device according to claim 1 wherein said telescopic engagement is compound form in that said two parts have respective male and female formations in mutual sliding engagement, said male formation has a bore therein defining said passageway, and said female formation includes a piston slidably engaged in said bore.

9. A device according to claim 8 wherein said piston is a separable part having a head slidably engaged in the remainder of said female formation and a rod slidably engaged in said male formation bore.

10. A device according to claim 8 wherein said passageway is of greater longitudinal extent than said piston, and said piston is at least of equal longitudinal extent to the remainder of said female formation.

* * * * *